(12) United States Patent
Masini

(10) Patent No.: US 6,225,523 B1
(45) Date of Patent: May 1, 2001

(54) INVERTIBLE WOUND DRESSINGS AND METHOD OF MAKING THE SAME

(76) Inventor: Michael A. Masini, 2950 Hickory La., Ann Arbor, MI (US) 48104

( * ) Notice: Subject to any disclaimer, the term of this patent is extended or adjusted under 35 U.S.C. 154(b) by 0 days.

(21) Appl. No.: 09/188,752

(22) Filed: Nov. 9, 1998

Related U.S. Application Data

(63) Continuation-in-part of application No. 08/886,792, filed on Jul. 1, 1997, now Pat. No. 5,833,646, which is a continuation-in-part of application No. 08/350,822, filed on Dec. 7, 1994, now Pat. No. 5,643,189.

(51) Int. Cl.[7] ............................. A61F 13/00; A61F 13/15
(52) U.S. Cl. ..................... 602/58; 604/358; 604/358.01; 604/358.19
(58) Field of Search .................... 604/385.01, 307, 604/385.06, 385.19; 128/849–856; 206/440, 441; 606/151, 213; 602/41–59; 294/1.3, 1.4, 1.5, 55

(56) References Cited

U.S. PATENT DOCUMENTS

| | | | |
|---|---|---|---|
| 3,369,545 | * | 2/1968 | Wanberg .......................... 604/385.1 |
| 3,604,423 | * | 9/1971 | Fraser ............................. 604/385.1 |
| 5,507,577 | * | 4/1996 | Fowler ................................. 383/7 |

* cited by examiner

Primary Examiner—Kim M. Lewis
(74) Attorney, Agent, or Firm—Gifford, Krass, Groh, Sprinkle, Anderson & Citkowski, PC

(57) ABSTRACT

A hospital type of bandage integrates an absorbent pad and non-stick layer with a fluid-impermeable outer layer and an adhesive in a single composite structure. In a preferred embodiment the invention further includes means which may be used to turn the bandage inside out upon removal, so that surfaces once contacting a patient are no longer externally exposed. A bandage according to the invertible embodiment preferably includes a pocket formed on the side of the bandage facing away from the patient after application, this pocket being large enough to accommodate at least a portion of a human hand, and inside this pocket and located opposite the entrance is a means for grasping which may be pulled outwardly through pocket opening, thereby inverting the entire structure. Various forms of devices for grasping are possible as alternatives, including a string, a tab and a tab with one or more finger-receiving holes. Means are further included for sealing the inverted structure, preferably in the form of a flap and associated adhesive.

8 Claims, 7 Drawing Sheets

INVERTIBLE WOUND DRESSINGS AND METHOD OF MAKING THE SAME

REFERENCE TO RELATED APPLICATION

This application is a continuation-in-part of U.S. patent application Ser. No. 08/886,792, filed Jul. 1, 1997 now U.S. Pat. No. 5,833,646, which is a continuation-in-part of U.S. patent application Ser. No. 08/350,822, filed Dec. 7, 1994, now U.S. Pat. No. 5,643,189.

FIELD OF THE INVENTION

The present invention relates generally to larger bandages of the type used, for example, in hospital settings and, more particularly, to a composite bandage with integrated absorbent, adhesive and fluid-impermeable layers. In a preferred embodiment the bandage may further be turned inside-out to self-contain surfaces once exposed to the patient.

BACKGROUND OF THE INVENTION

The AIDS epidemic, in particular, has caused medical personnel to take extreme precautions to avoid exposure to blood and other bodily fluids which might be infected. Doctors and dentists now wear rubber gloves and face masks in even the most routine situations, and various safety devices such as protective needles and so forth are being introduced with increasing frequency.

The removal of bandages and other wound dressings is an area where further safety measures are warranted. There are no composite wound dressings which integrate adhesive and absorbent layers in combination with a fluid impermeable cover. Instead, physicians routinely open a first sterilized pouch containing an absorbent pad and place that on the wound. Then rolls of sterilized tape are opened and, quite often, not only are the edges of the absorbent pad taped to the patient, but excessive tape is often used to cover the entire pad outer surface to ensure a fluid-tight seal. This is time consuming, and also results in multiple items requiring independent sterilization and considerable packaging waste.

The used bandages are discarded by placing them into specially marked bags which, in turn, are placed in specially marked disposal containers. This practice may expose associated personnel to dangerous pathogens since until such dressings are placed in their specially marked disposal containers, the surfaces once applied to the patient are outwardly unprotected. Also, there exists no consistent technique for placement within such bags, which may lead to contact with personnel during the process of insertion into the disposal bag or container.

SUMMARY OF THE INVENTION

The present invention solves problems associated with the application and disposal of wound dressings by providing a bandage which integrates an absorbent pad having a non-stick layer with a fluid-impermeable outer layer and adhesive in a single composite structure, so that only one item need be sterilized and accounted for. In a preferred embodiment, the invention further includes means which may be used to turn the bandage inside-out upon removal, so that surfaces once contacting a patient are no longer externally exposed. In this way, the bandage itself forms its own disposal pouch, thus solving the above-mentioned problems, including possible exposure during bandage removal and transfer, and further obviates the necessity for separate sterilized disposal vehicles.

In the invertible embodiment, a bandage according to the invention preferably includes a pocket formed on the side of the bandage facing away from the patient after application, this pocket being large enough to accommodate at least a portion of a human hand, preferably the entire hand. Inside this pocket and located opposite the entrance to the pocket is a graspable device which may be pulled outwardly through the pocket opening, thereby inverting the entire structure. Various forms of grasping means are possible as alternatives, including a string, a tab and a tab including one or more finger-receiving holes. Means are further included for sealing the bag once it is inverted, preferably in the form of a flap and associated adhesive. In the preferred embodiment this flap is also stiffened to be conveniently held by the hand not performing the actual inversion, with the two hands then cooperating for a smooth motion as the bandage structure is turned inside out. Other sealing means may be provided as alternatives, however, such as adhesive tape, a zip-lock type of fastener, or one or more semi-rigid but flexible cooperating elements disposed proximate to the pocket opening.

The semi-rigid or rigid flap is preferably folded near the mouth of the pocket prior to inversion so as to provide a stiffening proximate to the mouth of the pocket to help maintain structural integrity during inversion. The bandage may also include other, additional means to stiffen the mouth of the pocket opening and may further include some form of holding member extending outwardly from the side of the bandage at a point near to the entrance to the pocket, preferably in the form of a rigid or semi-rigid bar or stick-like protrusion which may be held by one hand while the bandage is inverted with the other. The protrusion may further be hingedly affixed to the side of the bandage to form a more compact structure until it is employed, and may fold over and seal the entrance to the pocket following inversion.

DETAILED DESCRIPTION OF THE INVENTION

Figure 1A:
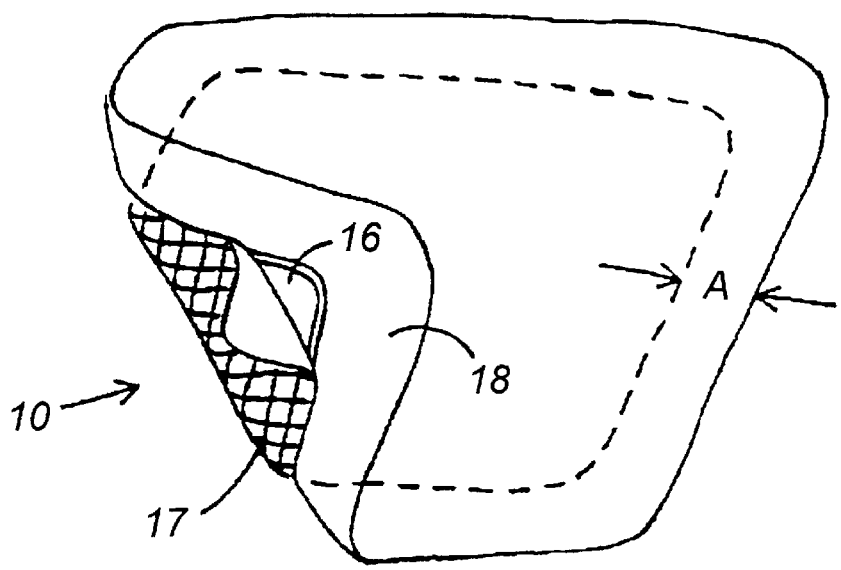
FIG. 1A is an oblique drawing of a bandage formed in accordance with this invention, with an area being folded over to show its absorbent and adhesive portions.

The present invention is directed toward bandages such as surgical dressings large enough to be used in post-operative situations, for example. Thus, bandages according to the invention range in size from a couple inches or so per side up to several inches per side, and are preferably rectangular in shape, in contrast to the small bandages and adhesive strips used for minor cuts and bruises. FIG. 1A shows at 10 a basic embodiment of a bandage formed according to the invention including an absorbent layer or pad 16 with non-stick layer 17 attached to a larger, fluid-impermeable layer 18. The layer 18 preferably extends beyond the pad 16 around its entire periphery by an amount depicted as "A," with at least a portion of this outwardly extending region of layer 18 including an adhesive at least between the pad and the outer edge of the layer 18 for securement to the patient.

In a preferred construction, a single fluid-impermeable layer 18 is provided with a relatively strong adhesive across the entirety of one of its two surfaces, which is used to hold the pad 16 to that surface with the remaining exposed peripheral portions with adhesive being used for patient contacting. Alternatively, further layers may be provided, such as a separate adhesive layer and fluid-impermeable layer. Although the figure shows substantially the same width of "A" around the entire periphery of the pad 16 and round corners, variations of these geometrical considerations are possible, as is non-rectangular overall shapes, such as ovals and circles, and so forth.

Preferably, the absorbent wound-contacting pad 16 includes a non-stick outer surface such as an Adaptic™-type layer (shown with hashed markings), which is popular in the profession since fluids may pass therethrough, but with the outer surface not adhering to the patient or wound. Also, in the preferred construction, at least the adhesive exposed for securement to the patient is preferably of the Microfoam type, as this is sufficiently strong enough to provide a good bond to the skin, but which is also flexible and tends to roll off the skin when lifted and pulled laterally, a feature which is advantageous for the invertible version of the bandage, as should be evident as discussed below. As with the variations possible in geometrical shape, variations in the use of the absorbent, adhesive and fluid-impermeable materials are also possible.

Figure 1B:
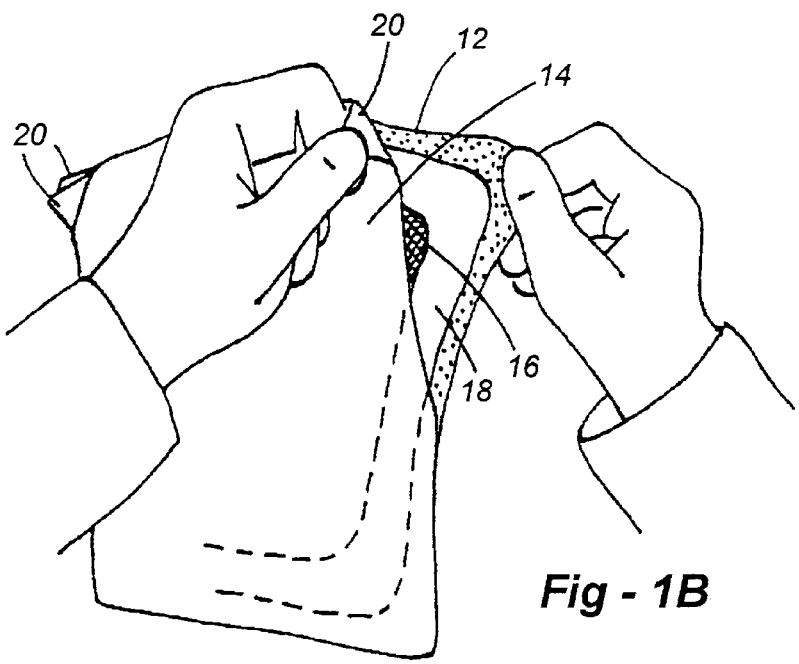
FIG. 1B is an oblique drawing illustrating a preferred form of packaging for a bandage constructed according to the invention.

FIG. 1B shows a preferred delivery method of the bandage of FIG. 1A, wherein two outer sheets 12 and 14 are used to entirely contain the bandage, and are accordingly the only materials that need to be discarded upon application. As shown in FIG. 1B, these outer layers 12 and 14, which may be of paper, foil, plastic or other alternative materials, are preferably slightly larger than the bandage itself and are sealed together beyond the extent of the bandage with an adhesive shown by the stippling, which releases as the two halves 12 and 14 are pulled apart as shown. The surface of the layer 14 facing the exposed adhesive portions of the bandage of layer 18 may further include a non-stick type of surface to ensure that the bandage does not stick to the packaging layer so as to cause problems upon removal. Dog-ear tabs 20 may further optionally be provided as a convenient grasping means for pulling apart the layers 12 and 14 during removal of the bandage 10.

Figure 2C:
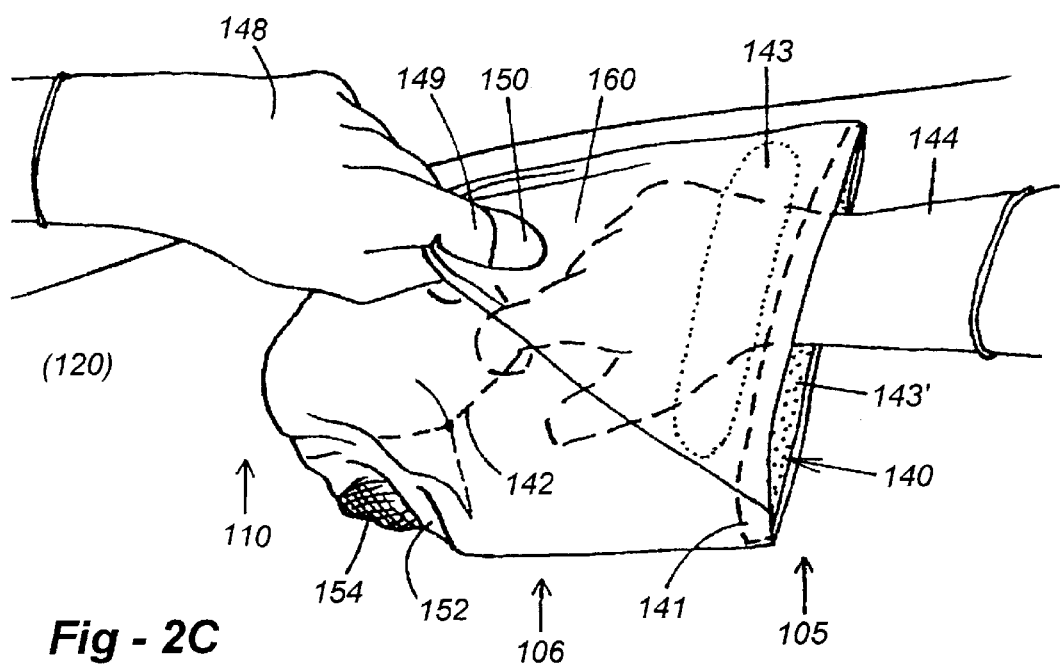
FIG. 2C is an oblique drawing of the invertible version of the bandage of FIG. 2B in the process of being inverted upon removal.
Figure 2A:
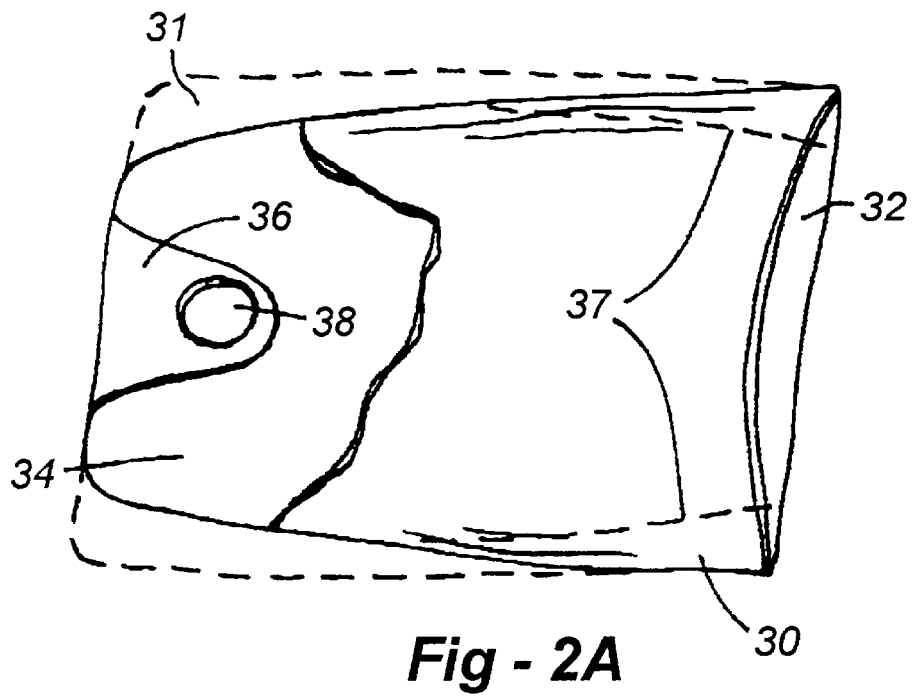
FIG. 2A is an oblique drawing of an invertible version of the bandage, with a portion of the outer layer being removed to expose a pull tab.
Figure 2B:
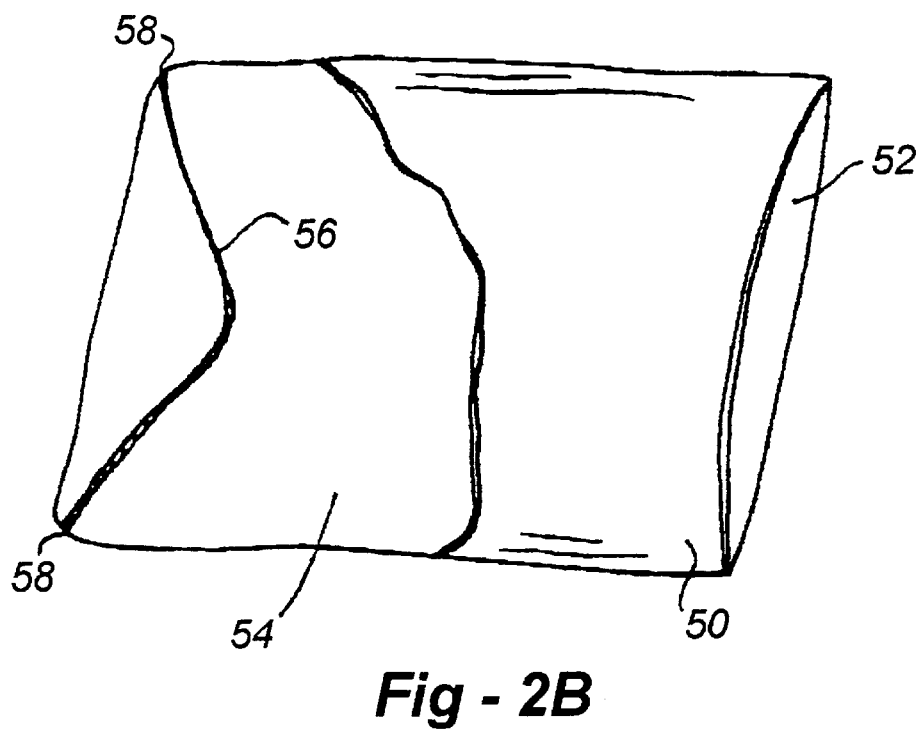
FIG. 2B is an oblique drawing of an invertible version of the bandage, with a portion of the outer layer being removed to show a string used for inversion.

FIGS. 2A–2C show embodiments of the bandage which enable it to be turned inside out upon removal, thus causing surfaces once contacting a patient to be pulled into an internal cavity formed during the inversion process. This capability reduces exposure to harmful pathogens in several ways, including the ability to dispose the bandage as soon as practically possible upon its removal from the patient, and elimination of the need for separate disposal bags and containers, which might cause accidents during bandage transfer.

FIG. 2A shows one embodiment of an invertible bandage structure having an outer layer 30 which forms a pocket on the surface of the bandage facing away from the patient after application. The pocket has an opening or mouth 32 at its proximal end and, inside the pocket at its distal end 34 there is bonded, attached or sewn some form of grasping means used for the inversion process. In FIG. 2A, with a portion of the outer layer 30 removed as shown, this grasping means takes the form of a tab 36 which may be flexible or rigid and which may or may not include one or more holes 38 into which a finger may be inserted.

To invert the bandage of FIG. 2A, the individual removing the bandage inserts at least a portion of the hand, preferably the entire hand, into the opening 32 of the pocket, grabs the tab 36, which is preferably centrally attached with respect to the distal end 34, and pulls the tab 36 out through the mouth 32, thus inverting the structure. In this particular embodiment, the overall shape of the bandage may beneficially be tapered away from a more rectangular form shown in broken lines 31. Such a tapered structure should assist in helping the inversion process to commence in a smooth manner. Additional tapering, as indicated by broken lines 37, may likewise optionally be provided. Although the tapering indicated by 37 may actually slightly increase the difficulty in inverting the structure midway through the inversion process, such a tapering might result in a final structure which is much more easily sealed into its contained, final form. As mentioned previously, geometrical considerations such as the size, shape and tapering of the bandage, are all options which remain in keeping with this invention, depending upon the size of the bandage, its application, and so forth.

FIG. 2B illustrates in oblique form yet another alternative version of the invertible embodiment of the invention, in this case a bandage 54 having an outer layer 50 which faces away from the patient when the bandage is applied, and a mouth formed on its proximal end. In contrast to the tab of FIG. 2A, however, the distal end has attached, sewn or otherwise bonded in its corners 58 a wire, cord or string 56. To remove this version of the bandage, a portion of the hand is inserted into the mouth 52 and the string 56 is grabbed with one or more fingers. One advantage of this configuration is that by pulling centrally on the string 56, the corners 58 naturally tend to move toward the center portion of the bandage proper, thus easing the inversion motion.

FIG. 2C shows, in oblique form, a bandage according to alternative 2B in the process of being inverted and removed from the patient 120. At its proximal end 105, the bandage includes an opening or mouth 140 into which at least a portion of an individual's hand is inserted. This opening 140 preferably including a flap 160 which may later be used to seal the bandage in its final inverted form. The flap preferably folds to an extent into the opening 140 at 141, thus advantageously creating a semi-rigid or substantially rigid edge along the top of the opening 140. Having the flap 160 initially folded into the mouth 140 prior to inversion assists in the inversion process, as does the rigidity resulting along the top edge of the opening 140.

The underside of the flap 160 as depicted in FIG. 2 preferably further includes an adhesive 143 which may serve various purposes. Prior to inversion, for example, this adhesive 143 may held to hold flap 160 down against the top surface of the upper layer forming the pocket. This adhesive action should not be too strong, however, since the flap 160 will need to release from this upper surface during the final stages of inversion. As such, a non-stick or reduced-tack surface may be provided directly beneath the adhesive 143 on the upper surface forming the top layer of the pocket to ensure that a release is achieved.

Once the bandage is fully inverted, this adhesive 143 will be used to seal the bag upon closure. In order to ensure a sufficient seal, a second adhesive region 143' may be provided corresponding to that of 143 in the correct area upon inversion such that the flap may be folded over and pressed thereagainst. For example, adhesive 143 and its accompanying adhesive area 143' may both be of the contact adhesive variety. Various other techniques are possible for the sealing of the bandage however, including a separate piece of tape, a zip-lock type of structure, and so forth, as previously mentioned. The adhesive area 143' also serves to hold the opening 140 closed until needed, but this adhesive action should not be strong enough to confound easy entry into the pocket. It is when adhesive areas 143 and 143' are brought together, as per FIG. 3, that bonding of the two surfaces preferably be substantial.

At the distal end 110 of the bandage 106 and internal to the pocket is some form of grasping means, in this case a string 142 attached at points 146 within the internal bandage structure, such as that depicted in FIG. 2B. The individual removing the bandage may thus grab the string 142 as shown with one or more fingers and pull in the direction of the pocket opening 140 to perform the inversion process. At the same time, as the one hand 144 of the individual inverting the bandage pulls on the string 142, the other hand 148 may conveniently grasp the distal end of the flap 160 with a finger 149 inserted through a hole 150 formed in the flap 160. As the string 142 is pulled, the internal distal ends 146 are pulled inwardly, so that the adhesive portion 152 and absorbent portion 154 are curled or otherwise deformed as the bandage is inverted these surfaces 152 and 154 being pulled into an inverted pouch created as the hands 144 and 148 are pulled apart from one another. Although the flap 160 is shown in generally triangular form with a rounded end other configurations are possible, and the number of holes 150 may be increased or decreased.

Figure 3:
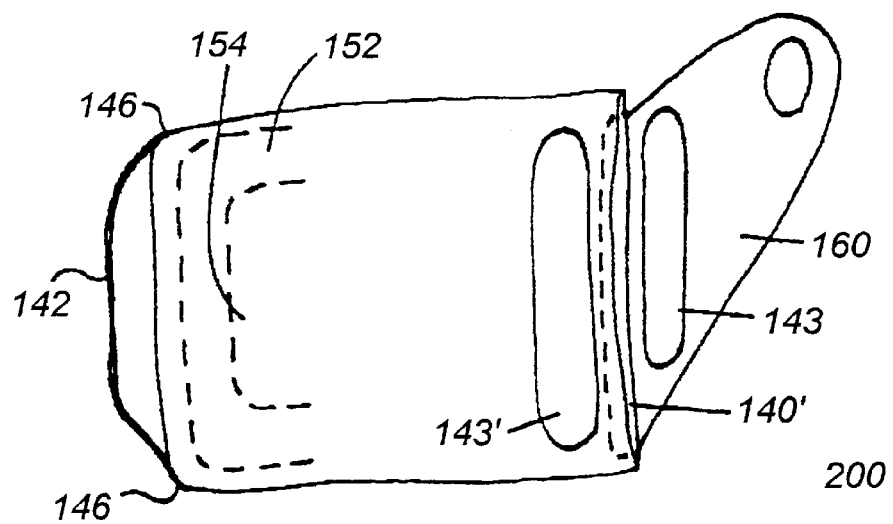
FIG. 3 is an oblique drawing of the invertible bandage in a final, inverted form.

FIG. 3 shows at 200 the bandage of FIG. 2C in its final inverted form. The string 142 will now be externally exposed and, indeed, may be used for convenient carrying. The flap 160 may now been folded over so as to seal the entrance through which the bandage was inverted. The broken lines 152 and 154 are used to indicate a portion of the patient contacting areas, which are now entirely enclosed within an internal cavity, with a new opening 140', formed through the inversion process. As seen in FIG. 3, the adhesive 143 on flap 160 may now be folded over so as to make contact with adhesive 143', thus sealing the inverted structure.

Figure 4:
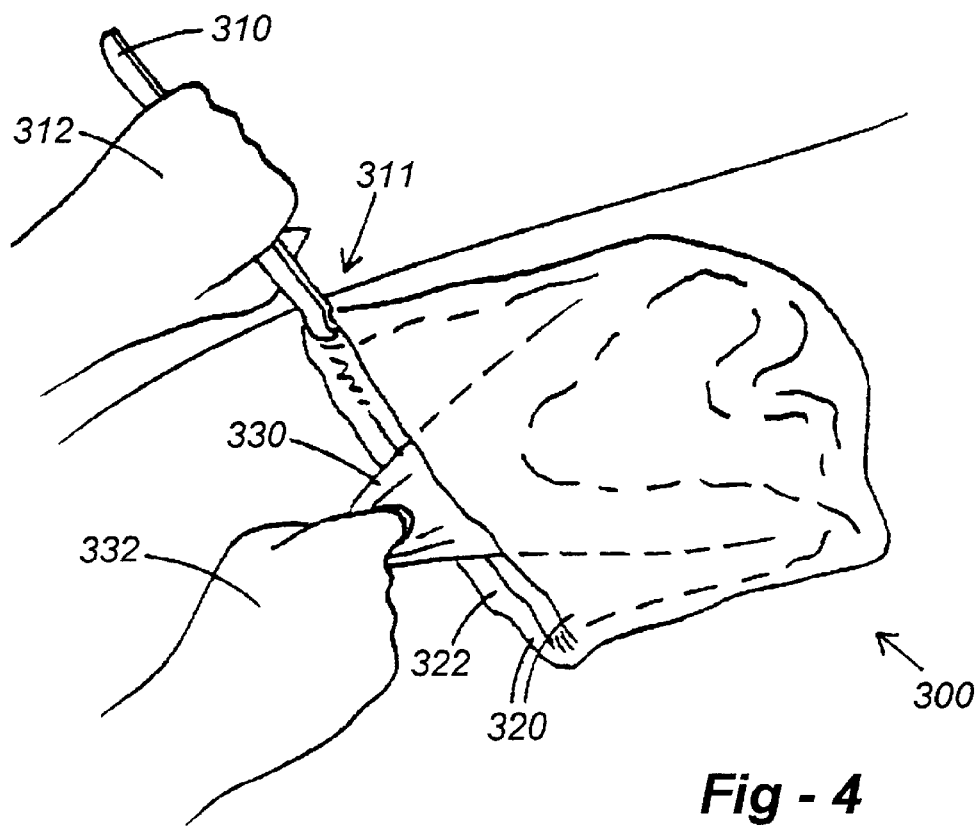
FIG. 4 illustrates an alternative embodiment of the invention including means for holding and stabilizing the opening of the pocket with one hand while performing the inversion operation with the other.

FIG. 4 illustrates the process of inverting yet a further alternative of the bandage, in this case including an optional protrusion in the form of a stick or bar 310 which may have a hinge 311 so that stick 310 may be used to seal the opening 322 prior to inversion and may additionally be folded back onto the opening of the inverted bandage to seal it in lieu of a flap or separate tape pieces. As shown, in operation, an individual removing the bandage 300 will grasp the stick 310 with a first hand 312 while grabbing the internal grasping means at the distal end of the bandage with his or her second hand 332. The grasping means in this case is a tab 330 having a hole to receive a finger of hand 332. In FIG. 3, the individual removing the bandage is partially through the process of inverting the same, such that the distal end of the bandage is now distorted as the tab 330 is being pulled between edges 320 which make up the opening 322. Edges 320 may further include embedded or external stiffening members (not visible in FIG. 4) which, in conjunction with the protruding stick 310, may alternatively further stabilize the opening 322 of the proximal end of the bandage until finally inverted. Stick 310 may be constructed and hinged in such a manner allowing it to be folded back over the open end to seal the internal cavity formed through the inversion process.

Figure 5:
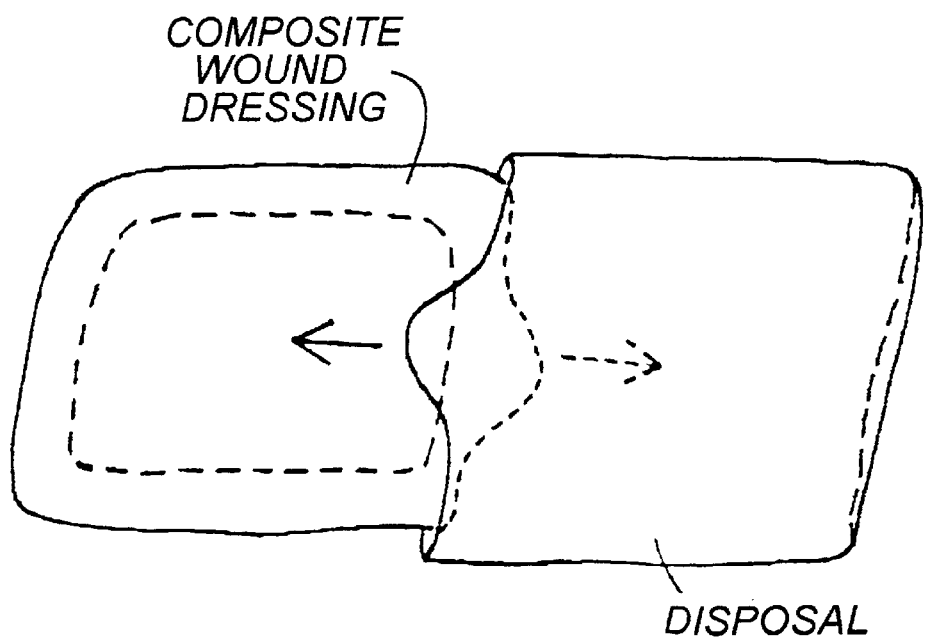
FIG. 5 is an oblique drawing of an alternative structure wherein the patient-contacting surface slider into an integral disposal pouch.

Broadly, in one embodiment, the present invention provides a composite structure for a bandage or wound dressing whereby a surface once contacting a patient may be subsequently contained in an integral disposal bag, pouch or cavity. Accordingly, it should be understood that numerous alternatives are possible beyond the invertible structures described and illustrated herein. One further alternative is shown in FIG. 5, where the patient-contacting layer slides into a disposal sleeve. Other possibilities include the folding and/or rolling up of the patient-contacting surface(s).

Figure 6A:
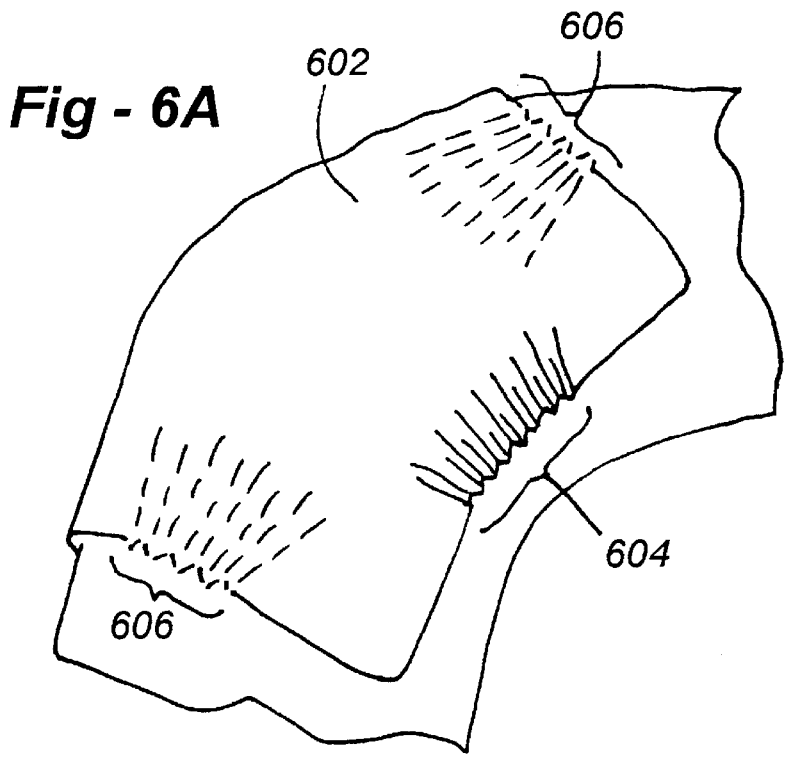
FIG. 6A illustrates an alternative embodiment of the present invention which shows gathering along a peripheral edge.
Figure 6B:
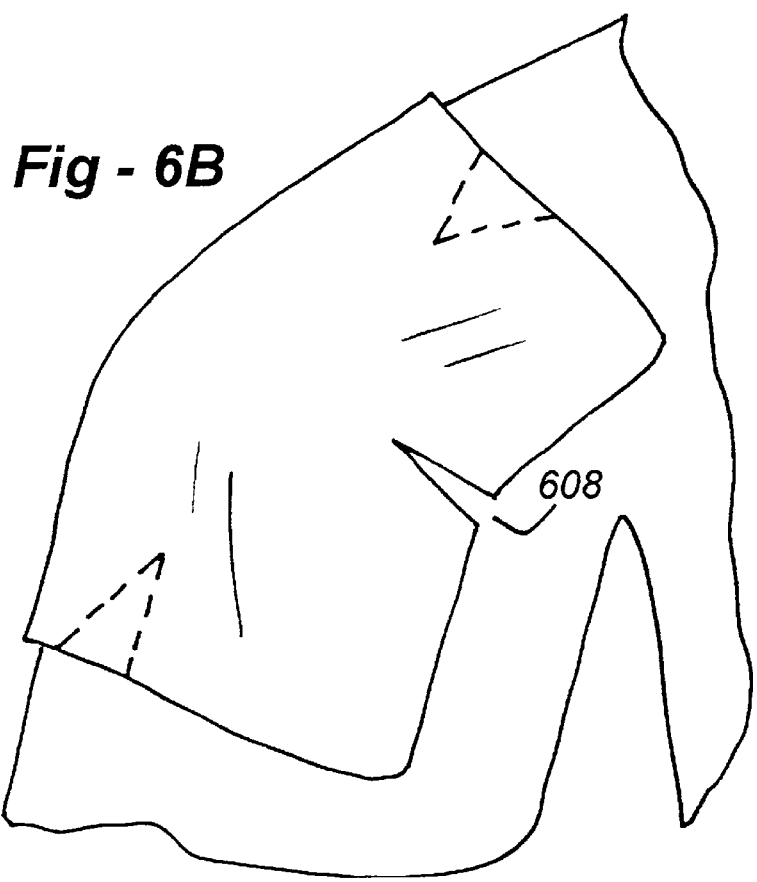
FIG. 6B illustrates a further embodiment of the invention which shows gathering in the form of one or more V-shaped notches on a peripheral edge.

FIGS. 6A and 6B illustrate alternative embodiments of a wound dressing according to the invention, wherein one or more of the peripheral edges of the dressing are prepared to permit a gathering thereof. Such gathering may be convenient in the presence of a non-planar patient surface, such as a shoulder or a knee, or in the event of a curved wound or incision, in which case the dressing may be articulated or bent within substantially the same plane. In addition, there may be situations in which both a curved patient surface and wound or incision or present, which would also benefit from such gathering.

FIG. 6A shows one gathering according to the invention wherein the wound dressing 602 includes one or more accordion-like sections 604, wherein, for example, at least a portion of at least one edge of the dressing is zig-zag-shaped, and which may, or may not, include an elastic member requiring stretching to ungather that section. Portion 606 has been shown in broken-line form to indicate that these gathered portions may be present on any or all of the edges of the dressing 602. In FIG. 6B, the means for gathering take the form of one or more V-shaped notches 608 which, again, may be provided in various locations, as indicated with the broken-line areas 610.

Figure 7A:
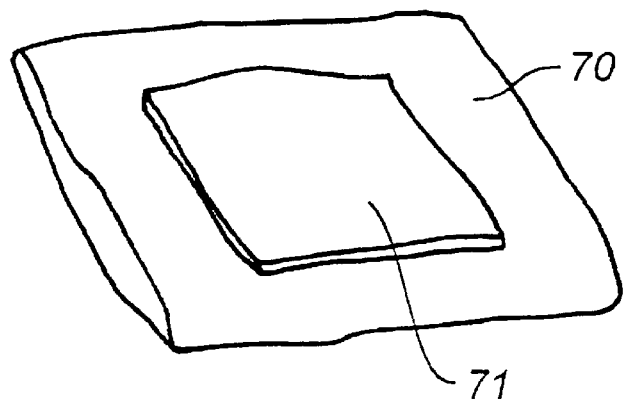
FIG. 7A illustrates an embodiment of the invention wherein a section of absorbent material is adhered to an existing bag structure having a larger area.
Figure 7B:
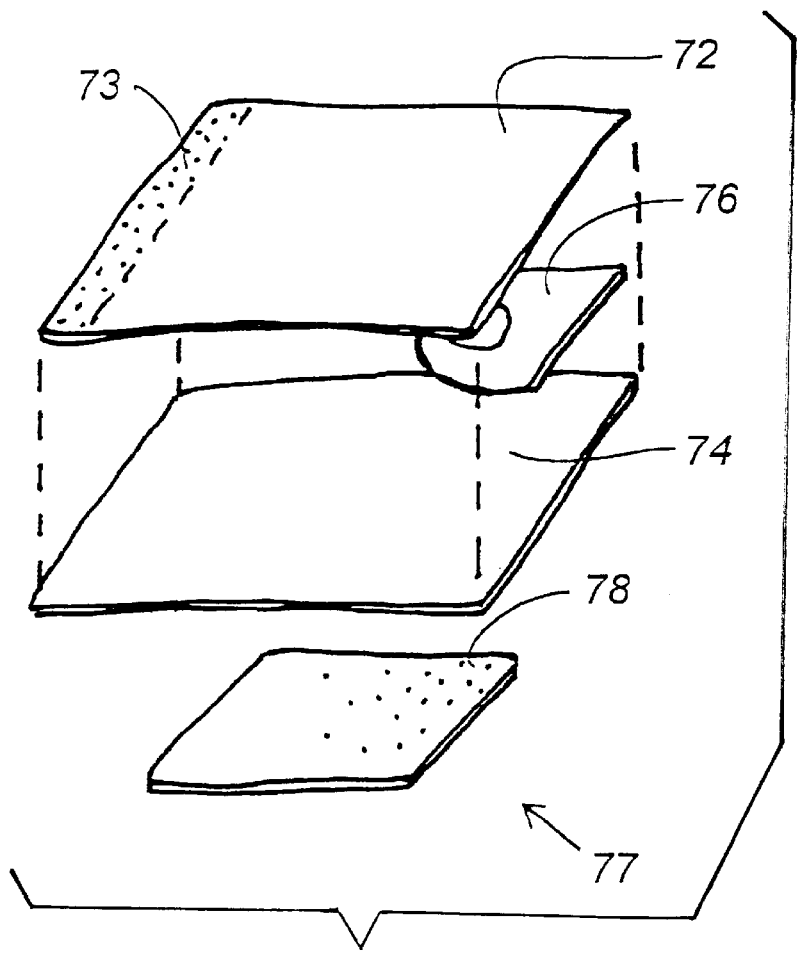
FIG. 7B is an exploded-view drawing illustrating steps that may be used to manufacture the embodiment of FIG. 7A in discrete form.
Figure 8:
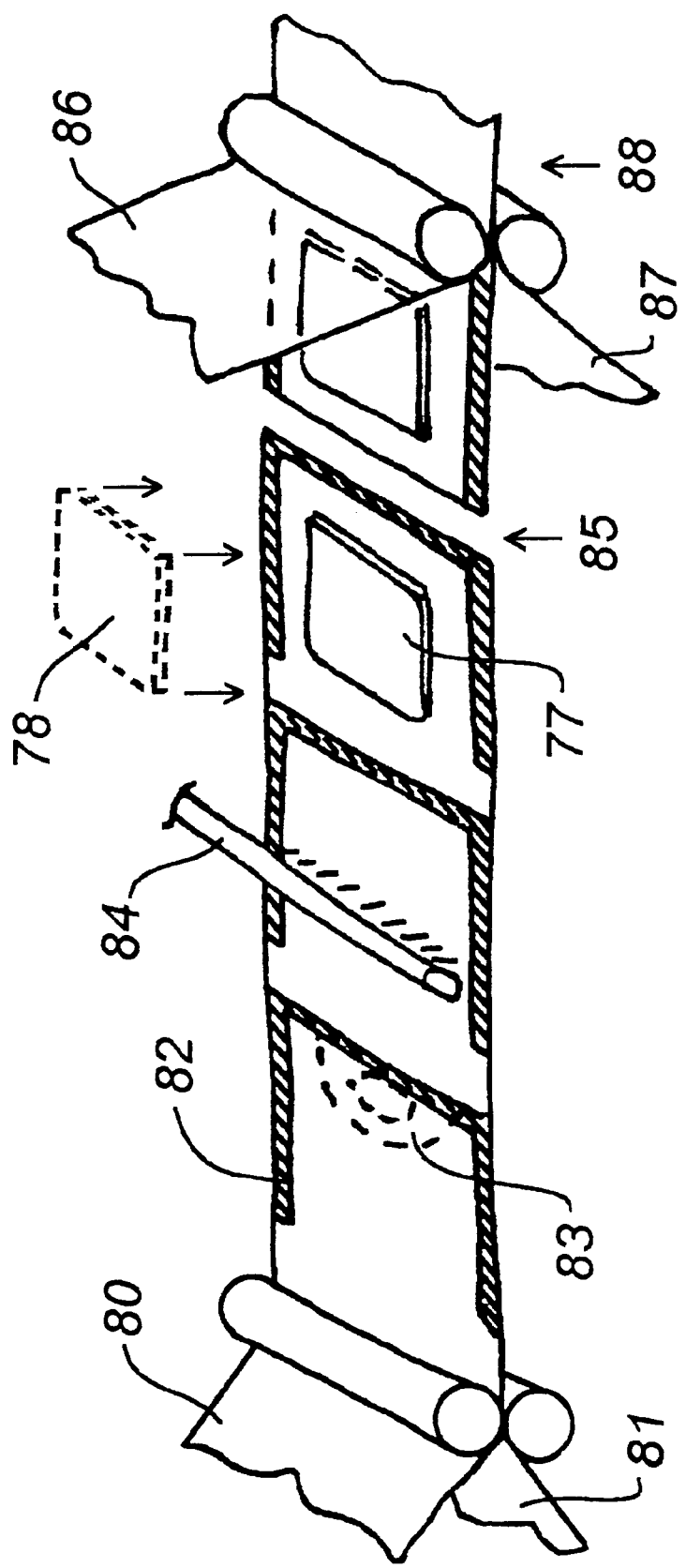
FIG. 8 illustrates a preferred method of manufacturing invertible bandages on a continuous web basis.

FIGS. 7 and 8 illustrate ways in which invertible wound dressings according to the invention may be fabricated. In particular, as illustrated obliquely in FIG. 7A one convenient approach is to adhere a piece of absorbent material 71 to an existing flattened bag 70 having an area peripherally larger than the material 71 to avail an exposed, body-contacting adhesive. The flattened bag 70, which is preferably constructed of fluid-impermeable material, may be realized in a number of ways, including partial folding and the use of peripheral adhesives and/or thermal welding, as depicted in FIG. 8.

Turning first to FIG. 7B, there is shown in an exploded view, structural components conducive to the assembly of FIG. 7A. In particular, a first pocket-forming sheet 72 is overlaid in co-extensive fashion with a second such sheet 74, optionally including an inversion-assist member such as pull-tab 76 therebetween. As best understood with reference to FIG. 8, three edges of the 72-74 pocket are joined, as through thermal welding, or the like, leaving an opening at one end, which would be leftward in FIG. 7B. The bottom or outwardly exposed surface of the sheet 74 receives an adhesive, to which a piece of absorbent material 77 may be attached. Preferably, since the material 77 has a smaller area than the 72-74 pocket, if adhesive is applied to the entire bottom surface of the bag, a peripheral area of adhesive will be left exposed for patient-contacting purposes, as discussed herein. In the event that the adhesive used for patient securement is insufficient to form a bond to the material 77, an additional adhesive 78 may be applied to the material 77, such that the marriage of the two adhesives results in a sufficiently substantial bond therebetween. The same holds true with the strip 73 of adhesive, which may be applied to the top side of the bag. Such an adhesive area 73 may not be that aggressive in terms of bonding power until the structure is inverted, at which time the area 73 will now be on the inside of the bag and in direct facing relation to a portion of the peripheral adhesive around the element 77, such that the user may compress these two areas for a tight seal.

FIG. 8 illustrates a preferred way in which embodiments of the invention described above may be carried out as part of a continuous web process. Broadly, noting that portions of the apparatus area left out for the purposes of clarity, an upper sheet 80 and a lower sheet 81 are fed between rollers into an area where a U-shaped bond 82 is formed as shown, optionally including inversion-assist means 83 which would have been dropped onto sheet 81 prior to the first set of rollers. Following this, an adhesive is applied through manifold 84, and a section of absorbent material 77 is dropped down from position 78 centrally onto the adhesive. As discussed above, the material 77 may or may not include an additional adhesive to assist with bonding to the upper adhesive-containing web 80. At 85, the web is cut to provide a space between wound dressings, and sterile layer/packaging sheets are applied via webs 86 and 87 through an additional set of rollers 88, after which individualized products may be severed and shipped to customers. Though not shown in FIG. 7B, bag closure means discussed elsewhere, such as adhesive strip 73 would be applied in a manner apparent to one of skill in the art prior to the second set of rollers and sterile encapsulation.

I claim:

1. A method of making an invertible wound dressing, comprising the steps of:

providing a flattened bag having a length and an opening sufficiently large to permit the entry of a human hand, and top and bottom outer surfaces defining an area;

providing a shaped piece of absorbent material having an area less than that of the bottom surface of the bag;

applying an adhesive to the bottom surface of the bag across an area larger than that of the absorbent material; and adhering the absorbent material to the bottom surface of the bag within the area having the applied adhesive.

2. The method of claim 1, wherein the adhesive is applied to the entire bottom surface of the flattened bag.

3. The method of claim 1, further including the step of applying an adhesive to the absorbent material prior to adhering the absorbent material to the bottom surface of the bag.

4. The method of claim 1, wherein the step of providing a flattened bag includes providing a bag having a lengthwise taper.

5. The method of claim 1, wherein the step of providing a flattened bag further includes the steps of:

providing upper and lower continuous webs of bag material;

joining the two webs through a U-shaped joint, such at the bottom of the U is transverse to the direction of the web and the top of the U forms the opening of the bag when the joined webs are severed.

6. The method of claim 1, further including the step of applying an adhesive to at least a portion of the top outer surface of the flattened bag proximate to the opening such that, upon inversion of the dressing, the adhesives on the top and bottom outer surfaces join together to seal the opening of the bag.

7. An invertible wound dressing, comprising:

a flattened bag having top and bottom outer surfaces defining an area, a lengthwise taper and an opening sufficiently large to permit the entry of a human hand, the lengthwise taper being such that the bag is wider at the opening to assist in helping the inversion process to proceed in a smooth manner; and a shaped piece of absorbent material bonded to the bottom surface of the bag and having an area less than that of the bottom surface.

8. The invertible wound dressing of claim 7, further including an adhesive applied to the bottom surface of the bag outside the area where the absorbent material is bonded to assist in securing the dressing to a recipient.

* * * * *